United States Patent [19]

Kojima

[11] Patent Number: 5,017,790

[45] Date of Patent: May 21, 1991

[54] TEMPERATURE CONTROLLER UNITS FOR DENTAL AGAR IMPORESSION MATERIALS

[75] Inventor: Norio Kojima, Tokyo, Japan

[73] Assignee: G-C Dental Industrial Corp., Tokyo, Japan

[21] Appl. No.: 414,304

[22] Filed: Sep. 29, 1989

[30] Foreign Application Priority Data

Nov. 2, 1988 [JP] Japan .................. 63-276090

[51] Int. Cl.$^5$ ............................................. G01N 23/00
[52] U.S. Cl. ........................................ 250/455.1; 422/24
[58] Field of Search ........................ 250/455.1; 422/24

[56] References Cited

U.S. PATENT DOCUMENTS

| | | | |
|---|---|---|---|
| 2,587,131 | 2/1952 | Ficken | 422/24 |
| 3,820,251 | 6/1974 | Abernathy | 422/24 |
| 4,114,024 | 9/1978 | Donner | 219/494 |
| 4,412,134 | 10/1983 | Herold et al. | 250/455.1 |
| 4,448,750 | 5/1984 | Fuesting | 250/455.1 |
| 4,771,162 | 9/1988 | Schatz et al. | 219/440 |
| 4,774,415 | 9/1988 | Biezel et al. | 250/494.1 |

Primary Examiner—Bruce C. Anderson
Attorney, Agent, or Firm—Oblon, Spivak, McClelland, Maier & Neustadt

[57] ABSTRACT

A temperature controller unit for dental agar impression materials is provided, which comprises in combination a box member having a lid disigned to be closed to shut off the outside air or prevent substantial entrance of the outside air, a heating device provided within the box member for heating the air within the box member to heat a dental agar impression material from a first heating temperature at which it is put in a complete sol state to a second heating temperature at which it remains in a sol state to take an intra-oral impression, a fan provided within the box member for circulating the air within the box member, a temperature detecting device provided within the box member for detecting the temperature of the air within the box member, a heating device controlling section provided within the box member for controlling the heating devices in receipt of a signal from the temperature detecting devices and a container holder provided within the box member for holding a plurality of containers filled therein with the dental agar impression material.

32 Claims, 3 Drawing Sheets

TEMPERATURE CONTROLLER UNITS FOR DENTAL AGAR IMPORESSION MATERIALS

BACKGROUND OF THE INVENTION

1. Field of the Invention

The present invention relates to a temperature controller unit for regulating to the desired heating temperature a dental agar impression material to be filled in a container, which is to be injected into a region to be subjected to impression taking in the oral cavity in dentistry.

2. Prior Art

In dentistry, the dental agar impression material to be injected into a region for taking an intra-oral impression is filled in a container such as a syringe for dental impression materials that takes the form of a solid rod at normal temperature and assumes the form of an injector or a cylindrical cartridge for dental impression materials that is closed up at one end with a rubbery membrane capable of forming easily a discharge port and fitted at the other end with a movable sealing piece. The dental agar impression material is heated to a first heating temperature (usually around 100° C.) through the container to put it into a complete sol state, and is then cooled down to and maintained at a second heating temperature (usually around 60° C.) at which an impression is to be taken giving no discomfort to patients. As occasion demands, the container is removed. In general, when the container is a syringe for dental impression materials, it may be used as such, whereas when the container is a cartridge for dental impression materials, it is attached for use to a syringe for the extrusion of dental impression materials designed exclusively therefor.

One system for heating and cooling such dental agar impression materials (hereinafter called the temperature controller unit for dental agar impression materials) has used boiling water as a heating medium for applying heat to the container filled therein with a dental agar impression material. With this type of system including a boiling water tank, the container having a dental agar impression material filled therein is charged into boiling water stored in the tank to heat it to the first heating temperature and, thereafter, cool and maintain it to and at the second heating temperature.

Another system available in the art has used a metallic body as a heating medium. With this type of system, the container having a dental agar impression material filled therein is brought (at the cylinder portion where the container is a syringe for dental impression materials or at the cylindrical portion where the container is a cartridge for dental impression materials) in contact with the metallic body including a heating source to heat the impression material to the first heating temperature and, thereafter, cool and maintain it to and at the second heating temperature.

Of such conventional temperature controller systems for dental agar impression materials as mentioned above, a problem with the former type is that if the dental agar impression material is heated from normal temperature at which it is solid to the first heating temperature to put it in a sol state and, then, cooled down to the second heating temperature at which they remain in a sol state through spontaneous cooling, then increased length of time is required to cool it to the second heating temperature, since high specific heat of water makes it difficult for hot water stored in the tank to cool down. For that reason, it is proposed to decrease the length of cooling time by incorporating relatively cold water, etc. into boiling water or providing another hot water tank in which stored is hot water maintained at the second heating temperature to keep the dental agar impression material in a sol state separately from the aforesaid boiling water-storing tank and transferring to said hot water tank the container having the dental agar impression material filled therein. However, such means for reducing the length of cooling time needs extra working steps that are time-consuming, and to handle the container in boiling water leads to a danger of a burn, etc. Additionally, it is unsanitary to maintain the hot water in the hot water tank at the second heating temperature for an extended period of time, since fungi tend to propagate. Moreover, it is uneconomical to provide two hot water tanks.

The latter type of system may not be used for some containers, although depending upon their dimensions and shape, since the portion of its metallic body to contact the containers is prescribed in terms of dimensions and shape. When the syringe for dental impression materials is used with this type of system, only its cylinder section comes in contact with the heating medium therefor, whereas its piston section serves as a heat radiator because of being not heated. As a consequence, the portion of the dental agar impression material in contact with the piston decreases in temperature and so tends to gel.

SUMMARY OF THE INVENTION

An object of the present invention is to solve the problems of such conventional temperature controller systems for dental agar impression materials.

According to the present invention, this object is achieved by the provision of a temperature controller unit for dental agar impression materials comprising in combination:

a box member having a lid designed to be closed to shut off the outside air or prevent substantial entrance of the outside air, heating means provided within said box member for heating the air within said box member to heat a dental agar impression material from a first heating temperature at which it is put in a complete sol state to a second heating temperature at which it remains in a sol state to take an intra-oral impression, a fan provided within said box member for circulating the air within said box member, temperature detecting means provided within said box member for detecting the temperature of the air within the said box member, a heating means controlling section provided within said box member for controlling said heating means in receipt of a signal form said temperature detecting means, and a container holder provided within said box member for holding a plurality of containers filled therein with said dental agar impression material.

With such a controller unit, it is possible to keep uniform and constant the peripheral temperature of the containers held in the box member, thereby applying uniform heat to the whole containers. Besides, since the heating means controlling section is provided to stop the operation of the heating means in receipt of a signal from the temperature detecting means such as a thermistor for detecting the interior temperature of the said box member, when the dental agar impression material filled in each container is cooled from the first heating temperature down to the second heating temperature, it is possible to carry out cooling in a short time owing to the specific heat of air being low and achieve various improvements in terms of safety and other factors.

BRIEF DESCRIPTION OF THE DRAWINGS

The present invention will now be explained in detail with reference to the accompanying drawings, which are given for the purpose of illustration alone, and in which.

DETAILED DESCRIPTION OF THE PREFERRED EMBODIMENTS

Figure 1:
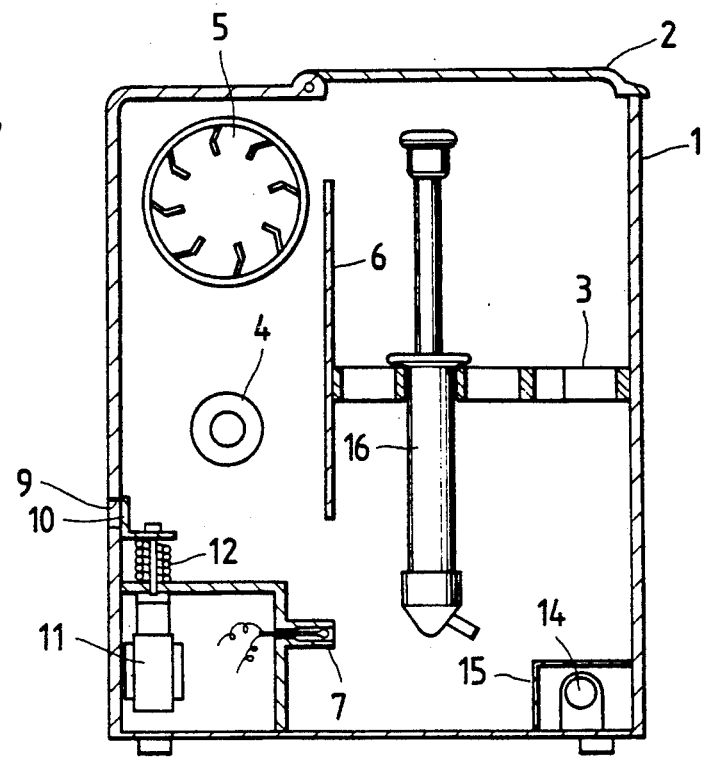
FIG. 1 is a sectional view of a syringe for dental impression materials which is held by the first embodiment of the temperature controller unit for dental agar impression materials according to the present invention.
Figure 2:
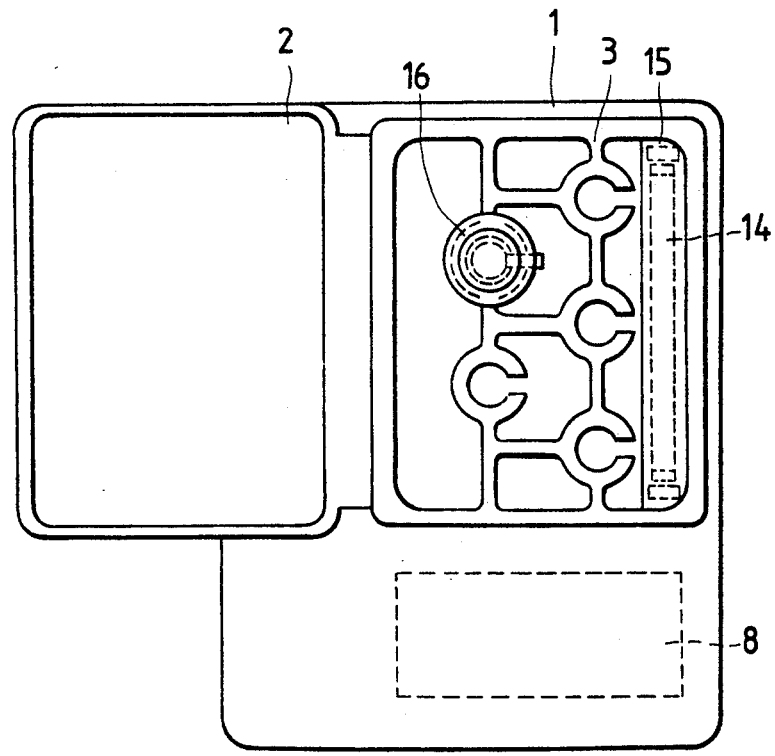
FIG. 2 is a plan view of FIG. 1 in which a lid is kept open.
Figure 3:
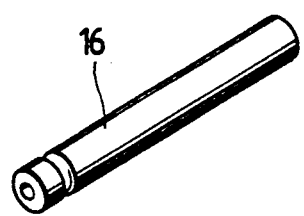
FIG. 3 is a perspective view of one example of a cartridge for dental impression materials.
Figure 4:
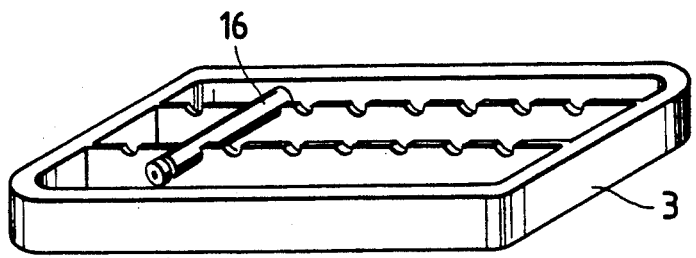
FIG. 4 is a perspective view of one cartridge for dental impression materials is held by one example of a container holder for dental impression material cartridges which is to be mounted in the temperature controller unit for dental agar impression materials according to the present invention.
Figure 6:
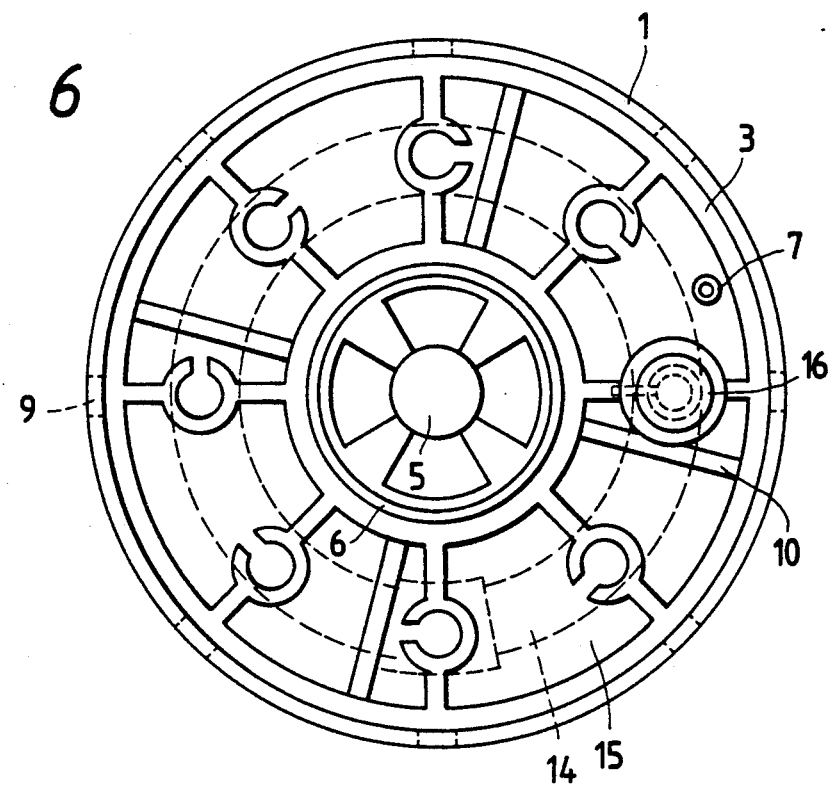
FIG. 6 is a plan view of FIG. 5 in which a lid is removed.
Figure 5:
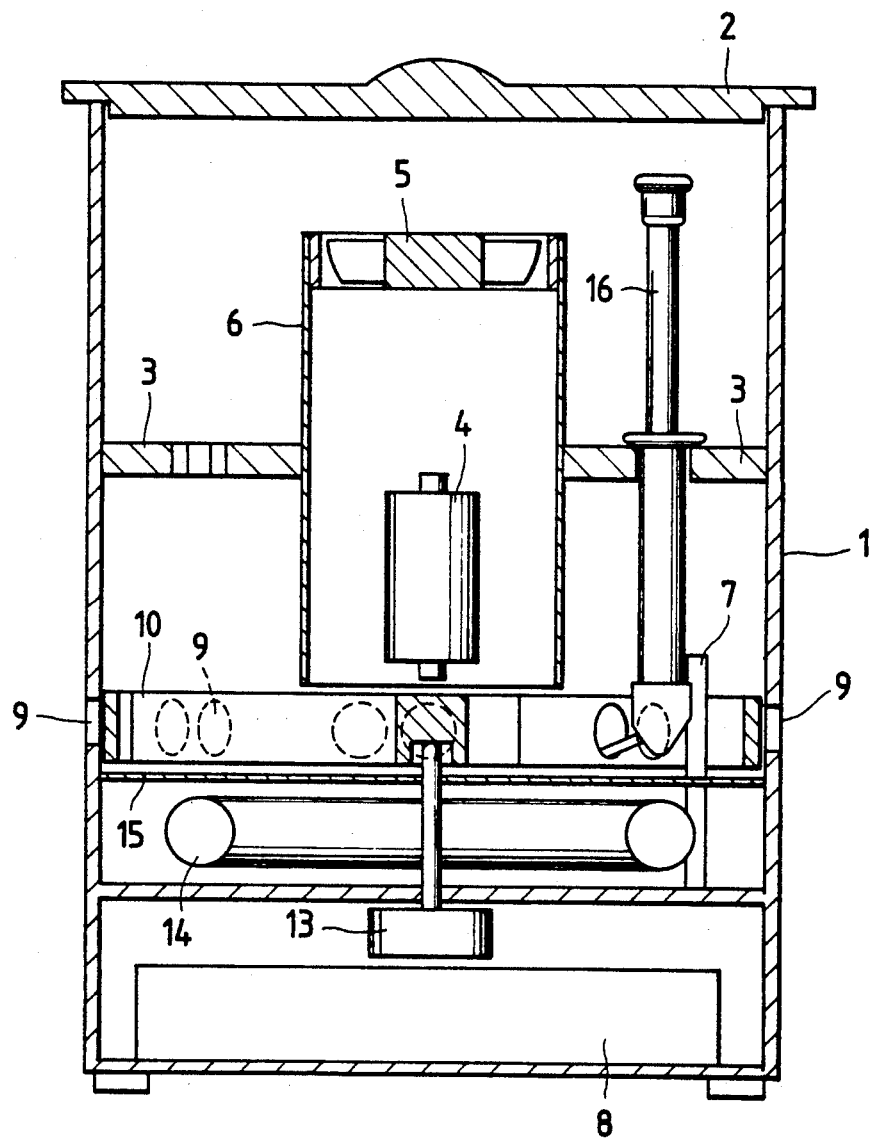
FIG. 5 is a sectional view of a syringe for dental impression materials which is held by another embodiment of the temperature controller unit for dental agar impression materials according to the present invention.

A box member 1 is in the predetermined form such as a rectangular or cylindrical form in section, and is preferably formed of a material excelling in a heat insulating effect. A lid 2 is mounted on the box member 1 to charge or discharge a container or containers 16 therein or therefrom. The box member 1 is of a structure that the outside air is shielded off or does hardly enter it in a lidded state. A container holder 3 is located within the box member 1 to hold the container 16 in place. Where the container 16 is in the form of a syringe for dental impression materials, the container holder 3 comprises a plurality of annuluses joined together by means of relatively thin rods, each of said annuluses being partly cut out to receive and easily hold the syringe 16, as illustrated in FIGS. 2 or 6. Where the container 16 is in the form of a cartridge for dental impression materials, the container holder 3 may comprise a plurality of annuluses joined together by means of relatively thin rods, each of said annuluses being partly cut out to receive and easily hold a necked portion of the cartridge, as is the case with the syringe for dental impression materials. Preferably, the container holder 3 may be of such a structure that the container 16 is laid on, as illustrated in FIG. 4. Preferably, the container holder 3 should be in the form capable of holding both the cartridges and the syringes, although not specifically illustrated. It is also preferred that the container holder 3 should be of a structure that it can be removed from within the box member 1 in its entirety, since it is then easy to replace the containers 16 depending upon whether they are in the form of cartridges or syringes and clean them. Heating means 4 is provided to bring the air prevailing in the box member 1 from the first heating temperature at which a dental agar impression material is put into a complete sol state to the second heating temperature at which it remains in a sol state to take an intra-oral impression. A fan 5 is provided to circulate the air heated by the heating means 4. Where the box member 1 is of a rectangular shape in section, as illustrated in FIG. 1, the fan 5 is preferably of a cross-flow type capable of feeding parallel flows of air. Where the box member 1 is of a cylindrical shape in section, as illustrated in FIG. 5, the fan 5 is preferably of an axial type capable of providing a radial circulation of air in the box member 1. A shielding plate 6 is located between the container holder 3 and the heating means 4, and is of a size such that radiant heat from the heating means 4 is shielded to prevent any local heating of the containers 16 held by the container holder 3 and of a structure such that air is transmittable from its both sides to assure smooth circulation of air in the box member 1. Temperature detecting means 7 such as a thermistor is provided to detect the temperature of the air circulating within the box member 1. A heating means controlling section 8 is provided to control the heating means 4 in receipt of a signal from the temperature detecting means 7 in such a manner that the heating means 4 is deenergized while the dental agar impression material is heated to the first heating temperature at which it is put into a complete sol state and cooled down to the second heating temperature at which it remains in a sol state to take an intra-oral impression and is later repeatedly energized or deenergized so as maintain the second heating temperature. There is provided a window 9 designed to be opened to feed the outside air in the box member 1 when the dental agar impression material is cooled from the first heating temperature down to the second heating temperature. More specifically, the window is opened immediately or sometime after it receives a signal from the temperature detecting means 7 upon its sensing that the air ciculating within the box member 1 reaches a preset maximum temperature at which the dental agar impression material is brought to the first heating temperature, and is closed upon reaching the second heating temperature. The opening or closing mechanism of this window 9 will now be explained with reference to the embodiment shown in FIG. 1. When the temperature detecting means 7 senses that the air circulating within the box member 1 reaches the preset maximum temperature at which the dental agar impression material is brought to the first heating temperature, an electrically operated solenoid 11 is actuated immediately or after lapse of preset time a signal therefrom is reached, thereby moving a window shielding plate 10 to open the window 9. Upon the second heating temperature being reached, the feed of power to the solenoid 11 is stopped to spring the window sheilding plate 10 back, shown at the spring 12. In the embodiment shown in FIG. 5, the box member 1 is of a cylindrical shape in section, and is provided in its side with a plurality of windows 9. When the temperature detecting means 7 senses that the temperature of air circulating within the box member 1 reaches a preset maximum temperature at which the dental agar impression material is brought to the first heating temperature, a stepping motor 13 is actuated immediately or after lapse of preset time it receives a signal from the temperature detecting means 7, thereby moving the window shielding plate 10 including ventilation holes along the inner wall of the box member 1 to open the windows 9. Upon the second heating temperature being reached, the stepping motor 13 is driven back for closing the windows 9. A germicidal lamp 14 is provided to apply ultraviolet rays to the container holder 3. Where the box member 1 is of a rectangular shape in section, as illustrated in FIG. 1, that lamp may be in the form of a straight tube or a spherical bulb. Where the box member 1 is of a cylindrical shape in section as shown in FIG. 5, however, it is preferably in the form of a circle. A covering 15 formed of a good transmittance of ultraviolet rays such as of quartz glass is provided to prevent the air circulating within the box member 1 from being in contact with the germicidal lamp 14.

In order to efficiently bring a dental agar impression material to the first heating temperature at which it is put in a complete sol state with the temperature controller unit for dental agar impression materials according to the present invention, which is of such a structure as detailed above, it is preferred in consideration of a temperature gradient prevailing in the container 16 in which the dental agar impression material is heated from its outside by thermal conduction, that the maximum temperature of the air heated by the heating means 4 is preset at somewhat higher than the first heating temperature, since the dental agar impression material is then permitted to reach the first heating temperature in a short time. Since no substantial proliferation of fungi occurs at such an elevated temperature as encountered while the air circulating within the box member 1 reaches the preset maximum temperature at which the dental agar impression material is brought up to the first heating temperature, it is unnecessary to light up the germicidal lamp 14 provided for the purpose of preventing the proliferation and killing of fungi present within the box member 1, especially fungi found in the oral cavity of a patient and on the containers 16 in touch with the hands of an operator or the outside air. Thus, the germicidal lamp 14 is designed to be put on only while the air circulating within the box member 1 in which fungi are likely to propagate is such that the dental agar impression material is maintained at the second heating temperature. In other words, the germicidal lamp 14 should preferably be put on immediately upon the temperature detecting means 7 producing a signal indicating that the air circulating within the box member 1 reaches a temperature at which the dental agar impression material is brought up to the second heating temperature.

Reference will now be made to how to use the temperature controller unit for dental agar impression materials according to the present invention, which is of a structure as stated above.

The lid 2 is first lifted to hold a plurality of the containers 16 filled therein with a dental agar impression material by the container holder 3. Then, the lid 2 is shut down to shield the interior of the box member 1 from the outside air or prevent substantial entrance of the outside air into the box member 1. Subsequent putting-on of a main switch (not shown) causes the fan 5 to be actuated (the fan 5 continues to work until operations terminate) to circulate the air within the box member 1 and, at the same time, the heating means 4 is actuated to increase the temperature of the air circulating within the box member 1. In this case, the provision of the shielding plate 6 between the container holder 3 and the heating means 4 assures that not only is radiant heat from the heating means 4 shielded off to prevent any local heating of the containers 16, but the circulation of air within the box member 1 takes place smoothly. Upon the air circulating within the box member 1 reaching the preset maximum temperature, the heating means 4 is immediately deenergized by the heating means controlling section 8 in receipt of a signal from the temperature detecting means 7. Alternatively, the heating means 4 is deenergized after the heating means 4 is controlled such that the air circulating within the box member 1 is maintained at the preset maximum temperature for a certain period of time. In this manner, the interior temperature of the box member 1 is decreased. In this case, if the window 9 is provided, then the window shielding plate 10 keeping the window 9 closed up is moved by the operation of solenoid 11 or stepping motor 13 to open the window 9, thereby providing an intake of the outside air. It is thus possible to cool the dental agar impression material from the first heating temperature down to the second heating temperature in a short time.

Where there is provided the germicidal lamp 14 for the irradiation of ultraviolet ray, it can be lit up to prevent the proliferation of fungi deposited on the containers 16 and kill them.

Where the germicidal lamp 14 is prevented from being in contact with the air circulating within the box member 1 through the covering 15 of good transmittance to ultraviolet rays, it is possible to prevent an increase in the temperature of the germicidal lamp 14, which may otherwise result in a drop of its efficiency or a reduction in its service life.

The temperature controller unit for dental agar impression materials according to the present invention, as detailed above, have various merits, as summarized below, and so makes a great contribution to dentistry.

(1) Since each container filled therein with a dental agar impression material is held in the box member in its entirety, it can be heated by the air circulating within the box member in its entirety. Accordingly, since there is no radiator acting upon the container, it is possible to uniformize the temperature of the dental agar impression material filled throughout the container, resulting in stable and effective use of the dental agar impression material to the last, thereof.

(2) Since the whole container is heated by the circulating air heated within the box member, it is possible to keep the peripheral temperature in the container uniform and constant regardless of its dimensions and shape.

(3) Since the whole container is heated by the circulating air heated within the box member, there is no need of incorporating relatively cold water into boiling water stored in the boiling water tank or transferring the container to another hot water tank, as carried out with some conventional systems, when cooling the dental agar impression material from the first heating temperature down to the second heating temperature. It is thus possible not only to eliminate a danger of a burn, etc. for increased safety, but also to reduce the number of operational steps involved.

(4) Where the box member is formed with the window adapted to be opened to provide an intake of the outside air when the dental agar impression material is cooled down to the second heating temperature, the window shielding plate is moved by the actuation of a solenoid or stepping motor immediately or some after receipt of a signal from the temperature detecting means indicating that the air circulating within the box member reaches the preset maximum temperature at which the dental agar impression material is brought up to the first heating temperature, whereby the window is kept open to take in the outside air. It is thus possible to decrease the temperature of the air circulating within the box member in a short time and, hence, reduce the length of cooling time.

(5) Where the shielding plate is interposed between the container holder for holding a plurality of the containers, each filled therein with a dental agar impression material, and the heating means to shield radiant heat from said heating means and permit air circulation from its both sides, it is possible to prevent any local heating of the container by radiant heat from the heating means and circulate air smoothly. It is thus possible to uniformize the temperature of the dental agar impression material throughout the container and make effective use thereof.

(6) The provision of the germicidal lamp for applying ultraviolet rays to the containers held by the container holder is very useful for improvements in sanitary conditions, since it is then possible to kill fungi deposited on the containers and present in the box member.

(7) Where the covering is provided to prevent the germicidal lamp from being in contact with the circulating air, it is possible to prevent the germicidal lamp from decreasing in its light output and service life by exposure to the circulating air of high temperatures.

(8) The container holders designed exclusively for syringes and/or cartridges for dental agar impression materilas may suitably be used depending upon the intended purposes.

What is claimed is:

1. A temperature controller unit for dental agar impression materials, comprising:
   a box member having a lid designed to be closed to shut off outside air or prevent substantial entrance of the outside air;
   heating means provided within said box member for heating air within said box member to heat a dental agar impression material from a first heating temperature at which it is put in a complete sol state to a second heating temperature at which it remains in a sol state to take an intra-oral impression;
   a fan provided within said box member for circulating the air within said box member;
   temperature detecting means provided within said box member for detecting the temperature of the air within said box member;
   a heating means controlling section provided within said box member for controlling said heating means in receipt of a signal from said temperature detecting means;
   a container holder provided within said box member for holding a plurality of containers filled therein with said dental agar impression material; and
   a shielding plate interposed between said container holder and said heating means for shielding said container from radiant heat provided by said heating means and permitting air circulation from both sides of said shielding plate, wherein localized heating of said containers is prevented.

2. A temperature controller unit as claimed in claim 1, wherein said container holder holds a plurality of syringes for dental impression materials of the containers filled therein with said dental agar impression materials.

3. A temperature controller unit as claimed in claim 2, wherein said box member is provided with a window which can be kept open to take in the outside air when said dental agar impression material is cooled down to said second heating temperature.

4. A temperature controller unit as claimed in claim 3, wherein a germicidal lamp is provided to apply ultraviolet rays to said containers held by said container holder.

5. A temperature controller unit as claimed in claim 2, wherein a germicidal lamp is provided to apply ultraviolet rays to said containers held by said container holder.

6. A temperature controller unit as claimed in claim 4, wherein a covering of good transmittance to ultraviolet rays is provided to prevent said germicidal lamp from coming in contact with the circulating air.

7. A temperature controller unit as claimed in claim 2, wherein said box member is provided with a window which can be kept open to take in the outside air when said dental agar impression material is cooled down to said second heating temperature.

8. A temperature controller unit as claimed in claim 7, wherein a covering of good transmittance to ultraviolet rays is provided to prevent said germicidal lamp from coming in contact with the circulating air.

9. A temperature controller unit as claimed in claim 2, wherein a germicidal lamp is provided to apply ultraviolet rays to said containers held by said container holder.

10. A temperature controller unit as claimed in claim 1, wherein said container holder holds a plurality of cartridges for dental impression materials of the containers filled therein with said dental agar impression materials.

11. A temperature controller unit as claimed in claim 10, wherein said box member is provided with a window which can be kept open to take in the outside air when said dental agar impression material is cooled down to said second heating temperature.

12. A temperature controller unit as claimed in claim 11, wherein a germicidal lamp is provided to apply ultraviolet rays to said containers held by said container holder.

13. A temperature controller unit as claimed in claim 10, wherein said box member is provided with a window which can be kept open to take in the outside air when said dental agar impression material is cooled down to said second heating temperature.

14. A temperature controller unit as claimed in claim 13, wherein a covering of good transmittance to ultraviolet rays is provided to prevent said germicidal lamp from coming in contact with the circulating air.

15. A temperature controller unit as claimed in claim 10, wherein a germicidal lamp is provided to apply ultraviolet rays to said containers held by said container holder.

16. A temperature controller unit as claimed in claim 10, wherein a germicidal lamp is provided to apply ultraviolet rays to said containers held by said container holder.

17. A temperature controller unit as claimed in claim 1, wherein said container holder holds a plurality of syringes and cartridges for dental impression materials of the containers filled therein with said dental agar impression materials.

18. A temperature controller unit as claimed in claim 17, wherein said box member is provided with a window which can be kept open to take in the outside air when said dental agar impression material is cooled down to said second heating temperature.

19. A temperature controller unit as claimed in claim 18, wherein a germicidal lamp is provided to apply ultraviolet rays to said containers held by said container holder.

20. A temperature controller unit as claimed in claim 17, wherein said box member is provided with a window which can be kept open to take in the outside air when said dental agar impression material is cooled down to said second heating temperature.

21. A temperature controller unit as claimed in claim 20, wherein a covering of good transmittance to ultraviolet rays is provided to prevent said germicidal lamp from coming in contact with the circulating air.

22. A temperature controller unit as claimed in claim 17, wherein a germicidal lamp is provided to apply ultraviolet rays to said containers held by said container holder.

23. A temperature controller unit as claimed in claim 20, wherein a germicidal lamp is provided to apply ultraviolet rays to said containers held by said container holder.

24. A temperature controller unit as claimed in claim 1, wherein said box member is provided with a window which can be kept open to take in the outside air when said dental agar impression material is cooled down to said second heating temperature.

25. A temperature controller unit as claimed in claim 24, wherein a germicidal lamp is provided to apply ultraviolet rays to said containers held by said container holder.

26. A temperature controller unit as claimed in claim 1, wherein said box member is provided with a window which can be kept open to take in the outside air when said dental agar impression material is cooled down to said second heating temperature.

27. A temperature controller unit as claimed in claim 26, wherein a germicidal lamp is provided to apply ultraviolet rays to said containers held by said container holder.

28. A temperature controller unit as claimed in claim 1, wherein a germicidal lamp is provided to apply ultraviolet rays to said containers held by said container holder.

29. A temperature controller unit as claimed in claim 28, wherein a covering of good transmittance to ultraviolet rays is provided to prevent said germicidal lamp from coming in contact with the circulating air.

30. A temperature controller unit as claimed in claim 1, wherein a germicidal lamp is provided to apply ultraviolet rays to said containers held by said container holder.

31. A temperature controller unit as claimed in claim 1, wherein said box member comprises a window for allowing the outside air to enter said box member, said window comprising means for opening said window to let in the outside air when said dental agar impression material is cooled down to said second heating temperature and closing said window when said dental agar impression material reaches said second heating temperature.

32. A temperature controller unit as claimed in claim 31, wherein said means for opening and closing said window is an electrically operated solenoid which is responsive to said temperature detecting means.

* * * * *

UNITED STATES PATENT AND TRADEMARK OFFICE
CERTIFICATE OF CORRECTION

PATENT NO. : 5,017,790

DATED : May 21, 1991

INVENTOR(S) : Norio Kojima

It is certified that error appears in the above-identified patent and that said Letters Patent is hereby corrected as shown below:

On the title page and col. 1, lines 1-2, should be --TEMPERATURE CONTROLLER UNITS FOR DENTAL AGAR IMPRESSION MATERIALS--.

Signed and Sealed this

First Day of December, 1992

Attest:

DOUGLAS B. COMER

*Attesting Officer*  *Acting Commissioner of Patents and Trademarks*